(12) United States Patent
Howie

(10) Patent No.: US 6,994,731 B2
(45) Date of Patent: Feb. 7, 2006

(54) PROSTHETIC IMPLANT

(76) Inventor: Donald W. Howie, 87 Seaview Rd., Tennyson, South Australia (AU) 5022

(*) Notice: Subject to any disclaimer, the term of this patent is extended or adjusted under 35 U.S.C. 154(b) by 0 days.

(21) Appl. No.: 10/154,691

(22) Filed: May 24, 2002

(65) Prior Publication Data

US 2002/0177901 A1 Nov. 28, 2002

(30) Foreign Application Priority Data

May 25, 2001 (AU) ........................ PR5263

(51) Int. Cl.
*A61F 2/36* (2006.01)

(52) U.S. Cl. ................................... 623/23.35

(58) Field of Classification Search .. 623/19.11–19.14, 623/20.14, 20.21, 20.32, 20.35, 20.36, 22.11, 623/22.4, 22.43, 23.15, 23.35; 606/60, 62, 606/63
See application file for complete search history.

(56) References Cited

U.S. PATENT DOCUMENTS

| | | | | |
|---|---|---|---|---|
| 4,030,143 A | * | 6/1977 | Elloy et al. ............... 3/1.91 |
| 4,357,716 A | | 11/1982 | Brown ...................... 3/1.913 |
| 4,608,055 A | | 8/1986 | Morrey et al. ............. 623/23 |
| 4,636,214 A | * | 1/1987 | Homsy ..................... 128/898 |
| 4,642,124 A | | 2/1987 | Cooke ..................... 623/23.17 |
| 4,657,552 A | * | 4/1987 | Karpf ....................... 623/23 |
| 4,670,015 A | | 6/1987 | Freeman ................... 623/23 |
| 4,718,909 A | | 1/1988 | Brown ...................... 623/16 |
| 4,728,334 A | | 3/1988 | Spotorno .................. 623/23 |
| 4,770,660 A | | 9/1988 | Averill ..................... 623/23 |
| 4,778,475 A | | 10/1988 | Ranawat et al. ........... 623/23 |
| 4,783,192 A | * | 11/1988 | Wroblewski et al. ...... 623/16 |
| 4,800,639 A | | 1/1989 | Frey et al. ................ 29/421.1 |
| 4,813,963 A | * | 3/1989 | Hori et al. ................ 623/23 |
| 4,851,004 A | * | 7/1989 | Homsy ..................... 128/898 |
| 4,871,369 A | * | 10/1989 | Muller ..................... 623/23.35 |
| 4,979,958 A | * | 12/1990 | Niwa et al. ............... 623/23.29 |
| 5,004,476 A | * | 4/1991 | Cook ....................... 623/23.3 |
| 5,035,713 A | | 7/1991 | Friis | |
| 5,037,425 A | | 8/1991 | Brown ...................... 606/92 |
| 5,041,141 A | * | 8/1991 | Ypma et al. .............. 623/23 |
| 5,047,061 A | | 9/1991 | Brown ...................... 623/23 |

(Continued)

FOREIGN PATENT DOCUMENTS

FR 2631543 * 11/1989

*Primary Examiner*—Eduardo C. Robert
*Assistant Examiner*—Anu Ramana
(74) *Attorney, Agent, or Firm*—Schwegman, Lundburg, Woessner & Kluth, P.A.

(57) ABSTRACT

A highly polished femoral implant (1) has a proximal neck portion (10), a distal tip portion (30), and an elongate stem portion (20) that extends from the neck portion to the tip portion. The stem portion (20) has a proximal or metaphyseal end region (21) which adjoins the neck portion (10), the proximal/metaphyseal end region (21) having a profile in the medio-lateral plane defined by a curved or angled medial outer contour and a curved or straight lateral outer contour. The stem portion (20) of the implant has a first part (24) adjacent said send region (21) having a profile in the medio-lateral plane which tapers distally at a first angle of taper to a region intermediate the length of the stem portion, and a second part (25,26) distal of the first part (24) having a profile in the medio-lateral plan which tapers distally at a second angle of taper from the region intermediate the length of the stem portion.

21 Claims, 1 Drawing Sheet

U.S. PATENT DOCUMENTS

| | | | |
|---|---|---|---|
| 5,108,452 A | 4/1992 | DeMane et al. ............... 623/23 |
| 5,152,799 A | 10/1992 | Lyons .......................... 623/23 |
| 5,156,627 A * | 10/1992 | Amstutz et al. ............. 623/23 |
| 5,171,275 A * | 12/1992 | Ling et al. .................... 623/16 |
| 5,314,494 A * | 5/1994 | Huiskes et al. ........... 623/23.35 |
| 5,480,450 A | 1/1996 | James et al. ................... 623/23 |
| 5,480,453 A * | 1/1996 | Burke ...................... 623/23.21 |
| 5,507,833 A * | 4/1996 | Bohn .......................... 623/23 |
| 5,658,349 A | 8/1997 | Brooks et al. ................ 623/23 |
| 5,746,771 A | 5/1998 | Clement et al. .............. 623/16 |
| 5,755,805 A * | 5/1998 | Whiteside ................ 623/23.24 |
| 5,755,811 A | 5/1998 | Tanamal et al. .............. 623/23 |
| 5,766,262 A | 6/1998 | Mikhail ........................ 623/23 |
| 5,776,204 A * | 7/1998 | Noble et al. .................. 623/23 |
| 5,951,563 A | 9/1999 | Brown ........................ 606/92 |
| 5,951,606 A | 9/1999 | Burke ........................ 623/23 |
| 5,954,771 A * | 9/1999 | Richelsoph et al. ..... 623/23.15 |
| 6,007,581 A * | 12/1999 | Noble et al. ............... 623/23.3 |
| 6,030,417 A * | 2/2000 | Bresler et al. ................. 623/23 |
| 6,383,226 B1 * | 5/2002 | Carter et al. ............. 623/23.21 |
| 6,383,228 B1 * | 5/2002 | Schmotzer ............... 623/23.35 |
| 6,524,343 B2 * | 2/2003 | Storer et al. ............. 623/23.46 |
| 6,702,854 B1 * | 3/2004 | Cheal et al. ............. 623/22.42 |
| 2003/0109933 A1 * | 6/2003 | Weissman et al. ....... 623/23.22 |

* cited by examiner

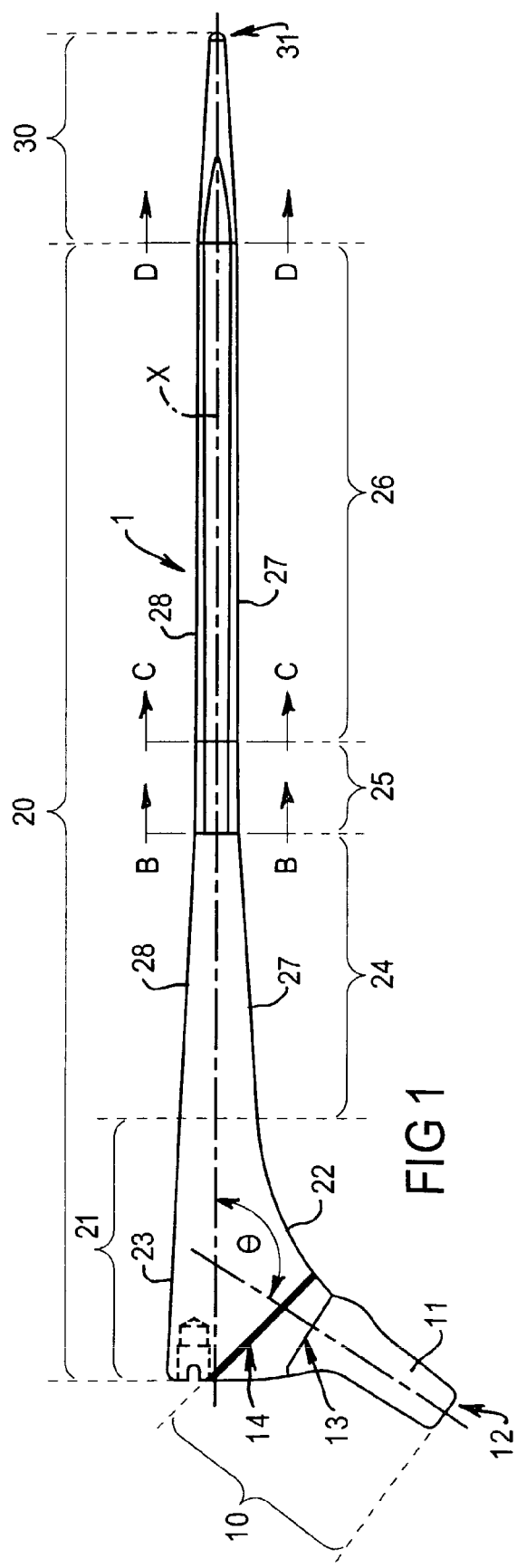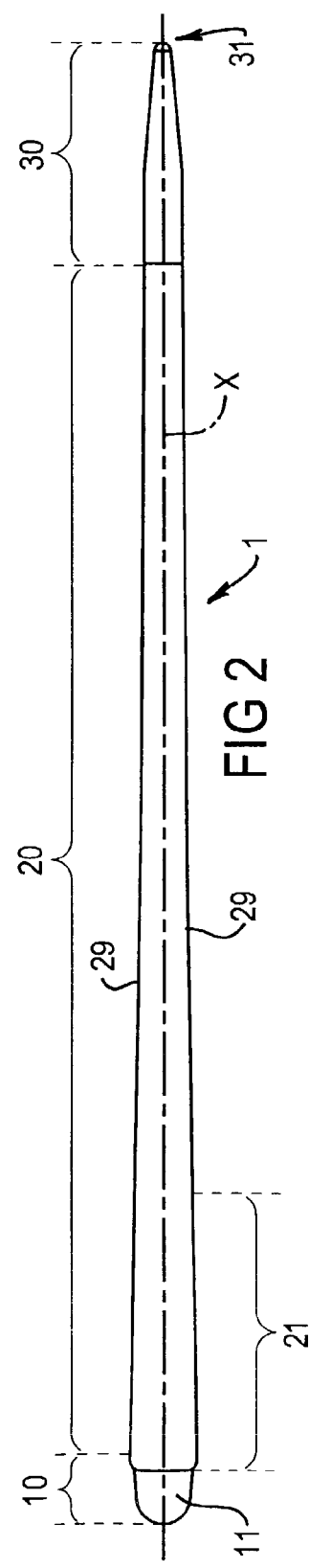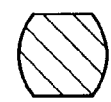

PROSTHETIC IMPLANT

FIELD OF THE INVENTION

The present invention relates generally to prostheses, and more particularly to an implant for a bone or joint prosthesis.

The invention has particular application to femoral implants for hip prostheses and it will be convenient to hereinafter describe the invention in this exemplary context. It should be appreciated, however, that the invention is not limited to this particular application, but is suitable for use in a range of other bones and joints. For example, the invention may also be suitable for knee, shoulder and elbow prostheses and may therefore include an implant for the tibia or humerus.

BACKGROUND OF THE INVENTION

Prostheses for use in total hip replacement typically include an elongate member for implantation in the femur. This implant member typically includes a distal tip portion for location deep within the bone, a proximal neck portion for providing articulation of the joint prosthesis and an elongate stem portion which extends from the distal tip portion to the proximal neck portion. In use, the elongate stem portion is also located within the bone to provide a foundation or support for the artificial joint and to transmit forces to the skeletal structure. The proximal neck portion of the implant projects from the end of the femur to form part of the articulated joint.

When looking at either the anterior or posterior surface of a femoral implant, the outer contour of the medial and lateral sides define the implant profile in the medio-lateral plane. When looking at either the medial or lateral surfaces of the implant, the outer contour of the anterior and posterior sides define the implant profile in the antero-posterior plane (i.e. the sagittal plane).

The stem portion of a femoral implant is typically integrally formed with the neck portion. Furthermore, the stem portion typically has a proximal end region adjacent the neck portion which, in use, is located within the proximal or metaphyseal end of the femur. The neck portion therefore joins the stem portion at this proximal or metaphyseal end region of the stem portion, and this metaphyseal end region of the stem typically has a profile in the medio-lateral plane that converges distally. That profile is typically defined by a curved or angled medial outer contour and a curved or straight lateral outer contour.

Because the implant members for hip prostheses are to be inserted into the femur, the stem portions of those implants need to be relatively narrow (particularly in their more distal parts) to fit within the intramedullary canal of the bone. This applies especially to longer implants (i.e. greater than 190 mm). Accordingly, the stem portion of an implant will typically taper in the medio-lateral plane, and possibly also in the sagittal plane, decreasing in transverse width towards the distal tip portion. In short or standard length implants, this tapering is often continuous along the length of the stem portion to the distal tip portion. In longer implants, however, in order to retain the desired structural integrity and function of the implant, the tapering will sometimes terminate at an approximately constant cross-section, which then continues to the distal tip portion of the implant.

A disadvantage of femoral implants with stem portions having a constant cross-sectional extent is that the constant cross-section part does not provide optimum transfer of loads to the surrounding bone structure in use. A further disadvantage of such implants is that they can be harder to extricate from their cemented position within the bone, in the event that the position or orientation of the implant requires revision at some later stage in the life of the prosthetic joint.

The present invention therefore aims to provide a new and improved prosthetic implant which substantially overcomes or at least ameliorates either or both of the above disadvantages.

SUMMARY OF THE INVENTION

According to a first aspect, the present invention provides an elongate prosthetic bone implant having a distal tip portion, a proximal neck portion and an elongate stem portion extending from the proximal neck portion to the distal tip portion. The stem portion of the implant is characterised by the fact that it has a first part having a profile in one of the medio-lateral and sagittal planes which tapers distally to a region intermediate the length of the stem portion at a first angle of taper, and a second part distal of the first part having a profile in that same one of the medio-lateral and sagittal planes which tapers distally from the region intermediate the length of the stem portion at a second angle of taper.

In the case of a femoral implant, the stem portion typically has a proximal end region adjacent the neck portion which, in use, is located within the proximal or metaphyseal end of the femur. As already noted, this metaphyseal end region of the stem portion typically has a profile in the medio-lateral plane defined by an angled or curved medial outer contour and a straight or curved lateral outer contour, with those outer contours tending to converge distally.

Accordingly, as far as the tapering profile of a femoral implant according to the invention concerns the medio-lateral plane, the first and second parts of the stem portion described above are located distally of the metaphyseal end region of the stem portion. The first part is preferably immediately adjacent and joins with the metaphyseal end region of the stem portion. As far as the tapering profile of a femoral implant according to the invention concerns the anterio-posterior (ie sagittal) plane, however, the first and second parts of the stem portion may be located at any position, including in the metaphyseal end region.

In a preferred embodiment of the invention, the tapering of the profiles of the first and second parts of the stem portion is substantially constant or linear over the length of the respective parts. That is, the first and second angles of taper don't substantially vary over the extent of the first and second parts of the stem portion, respectively.

Furthermore, the first and second angles of taper are preferably calculated relative to a longitudinal axis of the stem portion. That is, the angle of taper corresponds to the angle subtended by an outer contour of the stem portion in the particular one of the medio-lateral and sagittal planes and a longitudinal axis of the stem portion. Although larger angles are also contemplated, the first and second angles of taper are preferably between 0 degrees and about 10 degrees, and more preferably between 0 degrees and about 5 degrees. For example, a 1 degree or a 2 degree angle of taper in the first or second part of the stem portion is contemplated.

In a preferred embodiment of the invention, the profiles of the first and second parts of the stem portion taper substantially symmetrically.

In a preferred embodiment of the invention, the first angle of taper is greater than the second angle of taper.

In a preferred embodiment of the invention, the profile of the first part of the stem portion which tapers at the first angle, and the profile of the second part of the stem portion which tapers at the second angle are in the medio-lateral plane. In a particularly preferred embodiment of the invention, however, the stem portion also tapers in the antero-posterior plane. The angle of taper in the antero-posterior plane may be constant for both the first part and the second part of the stem portion. Alternatively, the first and second parts may again taper at differing angles. These differing angles may equal the first and second angles, respectively, or they may be entirely different.

In a preferred embodiment of the invention, the first part of the stem portion is substantially continuous with the second part of the stem portion. Accordingly, the stem portion may have no longitudinal extent in the intermediate region. Alternatively, however, the intermediate region may have some longitudinal extent and it may include no tapering in either or both of the medio-lateral and sagittal planes. This intermediate region could even have an extent of constant cross-section, but preferably there is no longitudinal extent of constant cross-section in the intermediate region. In a particularly preferred embodiment of the invention, the entire stem portion has no longitudinal extent having a constant cross-section. The tapering of the stem portion preferably continues to the distal tip portion.

In a preferred embodiment of the invention, the distal tip portion terminates in a rounded point, which is preferably relatively dull or blunt. The distal tip portion may itself also taper to that rounded point. This region forms an end of the implant, and may be designed to modify the loading at that end of the implant or to accept one of a variety of centralising devices.

In a preferred embodiment of the invention the stem portion may include a third part, distal of the second part, the profile of which in that same one of the planes again tapers distally at a third angle of taper different to the second angle of taper. The third angle of taper for this part of the stem portion is preferably less than the second angle of taper. The present invention also contemplates yet further tapering parts of the stem portion.

In a preferred embodiment of the invention, the transverse cross-sectional shape of the stem portion varies along its length. The cross-sectional shape of the first part of the stem portion is preferably a generally rectangular shape having rounded corners. The orientation of the rectangular cross-section of the first part is such that the medial, lateral, anterior and posterior surfaces of the first part of the stem portion are substantially flat surfaces. The second part, and subsequent parts (if any), of the stem portion preferably has a cross-sectional shape having opposite convexly arcuate curves inter-connected by two opposite parallel sides. In this respect, the convexly arcuate curves of the section shape correspond to convexly curved medial and lateral surfaces, while the opposite parallel sides of the section shape correspond to the substantially flat anterior and posterior surfaces.

In a preferred embodiment of the invention the cross-sectional shape of the distal tip portion also varies, transforming from the general configuration of the second or subsequent part of the stem portion to a generally circular cross-section at the extreme distal end of the tip.

The stem portion of the implant according to the invention preferably has a smooth, continuous outer surface. That is, the stem portion is preferably highly polished and devoid of any ridges, fin-like projections or other complex surfaces. In fact, the entire implant preferably has a smooth and continuous outer surface.

In a preferred embodiment of the invention, the proximal neck portion includes means for attaching a joint articulation device. In the case of a femoral implant for a hip-joint prosthesis, the means for attaching a joint articulation device includes a neck stub which projects at an angle in the range of between about 120° and 150° to the longitudinal axis of the stem portion. The neck stub is preferably a frusto-conical projection at a proximal end region of the neck portion and is adapted to receive a ball-shaped element of suitable diameter for engagement with either the patient's own acetabulum or a prosthetic acetabular cup element.

In a preferred embodiment of the invention, the proximal neck portion includes means for attaching a collar and/or spacer. The collar/spacer is adapted to assist in the positioning of the implant within the bone and also to transmit forces against a proximal end surface of the bone, from which the neck portion projects in use.

The proximal neck portion, stem portion and distal tip portion of the implant are typically integrally formed from stainless steel, titanium, or cobalt chrome molybdenum alloys, or other metals and metal alloys as known in the art. Furthermore, the stem portion of the implant is preferably overall generally straight.

In the case of femoral implants for hip prostheses, the boundary between the stem portion and the proximal neck portion of the implant can be thought of as being at the region where the implant is angled or curved medially to provide the correct angular orientation for the projecting neck stub—ie at the metaphyseal end region of the stem portion which has the curved or angled medial outer contour. Accordingly, the proximal neck portion may have a length in the range of 25 to 65 mm, while the distal tip portion may similarly have a length in the range of 30 to 60 mm.

The prosthetic implant of the present invention is preferably highly polished to provide relatively low shear forces when located in acrylic cement within the bone and to enhance the compression of the cement and any graft material employed. The implants of the invention are preferably fixed in position in the bone using an acrylic cement, or a combination of cement and bone graft or bone restoration material. However, cement may not necessarily be used.

Thus, in a preferred embodiment of the invention, the stem portion is adapted to enhance the distribution of stress through the acrylic cement to the bone graft or bone restoration material inserted within the femur to restore previous bone loss.

According to a second aspect, the present invention provides a joint prosthesis including an elongate prosthetic bone implant as described above. In particular, this invention preferably provides a hip prosthesis, which includes a femoral implant having the features described.

The present invention is therefore advantageously able to provide an elongate bone implant, and a joint prosthesis employing such an implant, having no regions of continuous cross-sectional extent. Rather, the invention is able to provide an implant for a joint prosthesis having a succession or series of tapered regions which enhance the fit of the implant within the bone, and enhance the compression or pressurization and thickness distribution of the cement mantle, while also improving the stress distribution to the bone and graft material for the prosthesis. Furthermore, the invention is able to provide an implant for a joint prosthesis having a succession or series of tapers which make the implant more easily removable. This is particularly so in the case of implants having a length greater than 190 mm, for example implants of 200 mm, 205 mm, 220 mm, 230 mm, 240 mm, 260 mm, 280 mm, 300 mm or even greater lengths.

It should be noted that the present invention does, however, also have application in standard or shorter length bone implants where the bones of the particular patient concerned have a relatively wide proximal cross-section but a relatively narrow more distal region. Prosthetic bone implants having a series of tapered regions according to the present invention may be designed to more optimally occupy or fill a bone having very narrow more distal dimensions.

BRIEF DESCRIPTION OF THE DRAWINGS

For assistance in arriving at a better understanding of the present invention, a preferred embodiment of a prosthetic implant according to this invention is hereafter described with reference to the accompanying drawings, in which:

FIG. 1 is a view looking at the anterior surface of a femoral implant for a hip prosthesis according to a preferred embodiment of the invention;

FIG. 2 is a view looking at the lateral surface of the femoral implant shown in FIG. 1.

FIG. 3 is a cross-sectional view of the stem portion of the implant in FIG. 1 in the direction of arrows B—B;

FIG. 4 is a cross-sectional view of the stem portion of the implant in FIG. 1 in the direction of arrows C—C; and FIG. 5 is a cross-sectional view of the stem portion of the implant shown in FIG. 1 in the direction of arrows D—D.

DETAILED DESCRIPTION OF THE PREFERRED EMBODIMENT

Referring to FIG. 1 of the drawings, the invention provides an integrally formed elongate femoral implant (1) having a proximal neck portion (10), an elongate stem portion (20) extending distally from the neck portion (10) and a distal tip portion (30). The implant (1) is for insertion within the intramedullary canal of a femur during hip-replacement surgery.

The proximal neck portion (10) includes a frusto-conical stub (11) projecting at the most proximal end region of the neck portion. This stub (11) has a free end (12) and continues from its other end (13) to join with the stem portion (20). A line (14) across the neck portion (10) effectively marks the extent of the neck portion, which in use projects from the proximal end of the femur. This line (14) also marks the point to which cement is applied when the implant is embedded in the femur.

The stub (11) provides means for attaching a ball-joint articulation device (not shown). Specifically, this conical stub (11) is adapted to receive a ball-shaped element for pivotal engagement within either the patient's own acetabulum or a corresponding prosthetic acetabular cup element. Furthermore, the stub (11) is oriented to project medially at a pre-determined angle (θ) in the range of 120° to 150° relative to a longitudinal axis (X) of the implant to suit the patient's physical proportions.

Immediately adjacent the neck portion (10), the elongate stem portion (20) of the implant (1) has a proximal or metaphyseal end region (21) which, in use, is located within the proximal or metaphyseal end of the femur. This metaphyseal end region (21) has a curved medial outer contour (22) and a straight lateral outer contour (23). Equally, however, the medial outer contour (22) could be angled, and/or the lateral outer contour (23) could be curved.

Furthermore, the elongate stem portion (20) includes a first part (24) which extends distally from the proximal end region (21) to an intermediate region of the stem. This intermediate region has effectively no longitudinal extent in this example, and a second part (25) of the stem portion extends distally from directly adjacent the first part (24). A third part (26) also extends distally of the second part (25). The third part (26) of the stem portion (20) continues in its extent to the distal tip portion (30).

Importantly, the stem portion (20) of the femoral implant (1) does not include any regions of longitudinal extent having a constant cross-section. The medio-lateral profile of the first part (24) of the stem portion (as seen in FIG. 1) tapers in the distal direction at a first angle of taper defined by the angle subtended between the longitudinal axis (X) and a medial outer contour (27) or a lateral outer contour (28). Furthermore, the second part (25) similarly tapers in the distal direction at a second angle of taper and the third part (26) tapers distally at a third angle of taper. In this particular example, the first angle of taper is larger than the second angle of taper which is, in turn, again larger than the third angle of taper.

Referring to FIG. 2 of the drawings, the profile of the stem portion (20) in the sagittal plane showing the anterior and posterior outer contours (29) also tapers in the distal direction. In this particular example, the profile of a length of the stem portion comprising the end region (21) and the first part (24) tapers in the sagittal plane at one angle, and the profile in this plane of a length of the stem portion comprising the second and third parts (25,26) tapers constantly at another lesser angle. In an alternative configuration, however, the angle of taper in the sagittal plane could be substantially constant along the entire length of the stem portion (20).

Referring now to FIG. 1 and FIGS. 3 to 5, it should also be appreciated that the cross-section of the stem portion (20) also varies along its length. The first part (24) of the stem portion has a substantially rectangular cross-section, with the flat sides of the rectangular-shaped cross-section corresponding to the flat anterior, posterior, medial and lateral surfaces of that part of the implant. The corners of the rectangular-shaped cross-section are rounded as shown in FIG. 3 and these rounded corners gradually transform over the length of the stem portion (20) to become the cross-sectional shape shown in FIG. 4. The cross-section shown in FIG. 4 reflects convexly curved medial and lateral outer surfaces of the stem portion and flat anterior and posterior surfaces. A similar but somewhat smaller cross-sectional shape is also shown in FIG. 5. The dimensions marked in FIGS. 3 to 5 are in millimeters and the change in height dimension from 10 mm in FIG. 3, to 9.8 mm in FIG. 4 and 8.5 mm in FIG. 5 reflects the tapering of the stem portion (20) in the medio-lateral plane between section lines B—B, C—C and D—D shown in FIG. 1, respectively.

The distal tip portion (30) of the implant continues to taper (albeit at an increased angle of taper) from the end of the third part (26) of the stem portion to the extreme distal point or tip (31). The relatively dull or blunt rounded point (31) is adapted to accept a centralising device for maintaining the tip in the desired position once the implant is inserted into the intramedullary canal.

It will be appreciated that various alterations and/or additions to the particular construction and arrangement of parts just described may be made without departing from the spirit or ambit of the present invention.

In this regard, for example, the stem portion (20) of the implant (1) may comprise merely a first part and a second part (i.e. no third part), with the first part corresponding to the first part (24) as shown in FIG. 1 and the second part corresponding to the third part (26) as shown in FIG. 1. In such a case, the intermediate region of the stem portion (20) might correspond to the part (25), the profile of which could for example be parallel (ie have no taper) in the medio-lateral plane while continuing to taper in the sagittal plane.

Alternatively, the stem portion (20) of the implant (1) may comprise merely a first part and a second part (i.e. no third part), with the first part corresponding to the first part (24) as shown in FIG. 1 and the second part corresponding to a combination of the second part (25) and third part (26) shown in FIG. 1. Again in this case, therefore, the intermediate region would have effectively no longitudinal extent.

What is claimed is:

1. An elongate, integrally formed prosthetic bone implant for cemented fixation within a bone, said implant having a distal tip portion, a proximal neck portion and an elongate stem portion extending from the neck portion to the tip portion, the stem portion having a proximal or metaphyseal end region which adjoins the neck portion, said end region tapering distally in the medio-lateral plane, wherein the stem portion of the implant has a first part adjacent said end region the proximal neck portion having a profile in at least one of the medio-lateral and or sagittal planes which tapers distally to a region intermediate the length of the stem portion at a first angle of taper, said first angle of taper being substantially constant along said first part, and a second part distal of the first part having a profile in that same at least one of the medio-lateral and or sagittal planes which tapers distally from the region intermediate the length of the stem portion at a second angle of taper, wherein the first angle of taper is greater than the second angle of taper said first and second parts extending substantially coaxially in the medio-lateral plane and said first part, said second part and said end region extending substantially coaxially in the anterior-posterior plane.

2. A prosthetic bone implant as claimed in claim 1 wherein the tapering of the profiles of the second part of the stem portion is substantially constant or linear over the length of the second part.

3. A prosthetic bone implant as claimed in claim 1, wherein the stem portion includes a third part, distal of the second part, the profile of which in that same at least one of the planes again tapers distally at a third angle of taper different to from the second angle of taper.

4. A prosthetic bone implant as claimed in claim 1, wherein the profile of the first part of the stem portion which tapers at the first angle and the profile of the second part of the stem portion which tapers at the second angle are in the antero-posterior plane.

5. A prosthetic bone implant as claimed in claim 1, wherein the profile of the first part of the stem portion which tapers at the first angle and the profile of the second part of the stem portion which tapers at the second angle are in the medio-lateral plane.

6. A prosthetic bone implant as claimed in claim 5, wherein proximal/metaphyseal end region of the stem portion has a profile in the medio-lateral plane defined by a curved or angled medial outer contour and a curved or straight lateral outer contour.

7. The implant according to claim 6, wherein the elongate stem portion is adapted to be cemented into a femur.

8. A prosthesis including an elongate prosthetic bone implant as claimed in claim 1.

9. The prosthetic bone implant as claimed in claim 1, wherein the stem extends along a longitudinal axis and the first and second parts taper distally about the axis.

10. The prosthetic bone implant as claimed in claim 1, wherein the distal tip portion is adapted to be cemented into a femur.

11. The prosthetic bone implant according to claim 1, wherein the second part includes a posterior surface that is planar and an anterior surface that is planar.

12. The prosthetic bone implant according to claim 11, wherein the posterior surface is parallel to the anterior surface.

13. The prosthetic bone implant according to claim 12, wherein the first part includes a posterior surface that is planar and an anterior surface that is planar, and wherein the posterior surface of the first part and the anterior surface of the first part are parallel.

14. The prosthetic bone implant according to claim 11, wherein the second part includes a lateral surface that is convexly curved and a medial surface that is convexly curved.

15. The prosthetic bone implant according to claim 1, wherein the stem portion is adapted to transfer axial loads to the bone in which the stem portion is implanted via a cement with which the stem portion is fixed to the bone.

16. A highly polished femoral implant having a proximal neck portion, a distal tip portion, and an elongate stem portion extending from the neck portion to the tip portion, the stem portion having a proximal or metaphyseal end region which adjoins the neck portion, the proximal/metaphyseal end region of the stem portion having a profile in the medio-lateral plane defined by a curved or angled medial outer contour and a curved or straight lateral outer contour, said end region tapering distally in the medio-lateral plane, wherein the stem portion of the implant has a first part adjacent said end region having a profile in the medio-lateral plane which tapers distally at a first angle of taper to a region intermediate the length of the stem portion, said first angle of taper being substantially constant along said first part, and a second part distal of the first part having a profile in the medio-lateral plane which tapers distally at a second angle of taper from the region intermediate the length of the stem portion, wherein the first angle of taper is greater than the second angle of taper, said first and second parts extending substantially coaxially in the medio-lateral plane and said first part, said second part and said end region extending substantially coaxially in the anterior-posterior plane.

17. A femoral implant as claimed in claim 16 wherein the stem portion has a profile in the antero-posterior plane which also tapers in the distal direction in each of the first and second parts of the stem portion.

18. A femoral implant as claimed in claim 17 wherein the profile in the antero-posterior plane tapers in the distal direction at a constant angle over the entire length of the stem portion.

19. A femoral implant as claimed in claim 17 wherein the profile in the antero-posterior plane tapers in the distal direction at different angles in the first part and the second part of the stem portion, respectively.

20. A femoral implant as claimed in claim 16, wherein the stem portion includes a third part, distal of the second part, the profile of which in the medio-lateral plane again tapers distally at a third angle of taper different to from the second angle of taper.

21. A hip prosthesis including a femoral implant as claimed in claim 16.

* * * * *